US012186173B2

(12) United States Patent
Glaug et al.

(10) Patent No.: US 12,186,173 B2
(45) Date of Patent: Jan. 7, 2025

(54) FASTENING SYSTEM FOR ABSORBENT ARTICLES

(71) Applicant: Drylock Technologies NV, Zele (BE)

(72) Inventors: Frank Glaug, Eau Claire, WI (US); Ricardo Borrero, Eau Claire, WI (US)

(73) Assignee: Drylock Technologies NV, Zele (BE)

( * ) Notice: Subject to any disclaimer, the term of this patent is extended or adjusted under 35 U.S.C. 154(b) by 379 days.

(21) Appl. No.: 16/468,554

(22) PCT Filed: Nov. 24, 2017

(86) PCT No.: PCT/EP2017/080363
§ 371 (c)(1),
(2) Date: Jun. 11, 2019

(87) PCT Pub. No.: WO2018/108485
PCT Pub. Date: Jun. 21, 2018

(65) Prior Publication Data
US 2019/0307616 A1    Oct. 10, 2019

Related U.S. Application Data

(60) Provisional application No. 62/432,729, filed on Dec. 12, 2016.

(51) Int. Cl.
*A61F 13/514* (2006.01)
*A61F 13/56* (2006.01)

(52) U.S. Cl.
CPC .... *A61F 13/5638* (2013.01); *A61F 13/51401* (2013.01); *A61F 2013/51441* (2013.01);
(Continued)

(58) Field of Classification Search
CPC .......... A61F 13/51401; A61F 13/51476; A61F 13/51478; A61F 13/51484; A61F 13/5622;
(Continued)

(56) References Cited

U.S. PATENT DOCUMENTS 5,611,791 A    3/1997  Gorman et al.
5,735,840 A *  4/1998  Kline ................ A61F 13/15756
                                                604/391

(Continued)

FOREIGN PATENT DOCUMENTS

WO    WO-9916400 A1    4/1999
WO    WO-2017158185 A1    9/2017

OTHER PUBLICATIONS

"International Application Serial No. PCT/EP2017/080363, International Search Report dated Feb. 12, 2018", (Feb. 12, 2018), 4 pgs.

(Continued)

*Primary Examiner* — Catharine L Anderson
(74) *Attorney, Agent, or Firm* — Schwegman Lundberg & Woessner, P.A.

(57) ABSTRACT

The present invention is a disposable absorbent undergarment, such as an adult brief or baby diaper, having an exterior surface designed to provide improved attachment for one or more fastener members, thereby resulting in improved closure and securement of the undergarment to a wearer.

23 Claims, 6 Drawing Sheets

(52) U.S. Cl.
CPC .............. *A61F 2013/51452* (2013.01); *A61F 13/51476* (2013.01)

(58) Field of Classification Search
CPC .... A61F 13/5638; A61F 13/565; A61F 13/62; A61F 13/622; A61F 13/625; A61F 13/627; A61F 2013/49023; A61F 2013/49025; A61F 2013/51441; A61F 2013/51452; A61F 2013/5147
See application file for complete search history.

(56) References Cited

U.S. PATENT DOCUMENTS

| | | | | |
|---|---|---|---|---|
| 6,572,602 | B2* | 6/2003 | Furuya | A61F 13/51496 604/385.03 |
| 6,589,638 | B1* | 7/2003 | McCormack | A61F 13/627 428/198 |
| 7,833,917 | B2* | 11/2010 | Shelley | B32B 5/08 442/149 |
| 8,722,963 | B2* | 5/2014 | Kanya | A61F 13/51476 604/380 |
| 2004/0203309 | A1* | 10/2004 | Allen | D04H 3/16 442/361 |
| 2006/0148354 | A1 | 7/2006 | Shelley et al. | |

OTHER PUBLICATIONS

"International Application Serial No. PCT/EP2017/080363, Written Opinion dated Feb. 12, 2018", (Feb. 12, 2018), 9 pgs.

\* cited by examiner

FASTENING SYSTEM FOR ABSORBENT ARTICLES

PRIORITY APPLICATIONS

This application is a U.S. National Stage Filing under 35 U.S.C. 371 from International Application No. PCT/EP2017/080363, filed on Nov. 24, 2017, and published as WO2018/108485 on Jun. 21, 2018, which claims the benefit of priority to U.S. Provisional Application No. 62/432,729, filed on Dec. 12, 2016; the benefit of priority of each of which is hereby claimed herein, and which applications and publication are hereby incorporated herein by reference in their entirety.

FIELD

The present disclosure relates generally to disposable absorbent articles, and, more particularly, to a disposable adult brief or baby diaper having an exterior surface designed to provide improved attachment for one or more fastener members, thereby resulting in improved closure and securement of the article to a wearer.

BACKGROUND

There are several types of commercially available products for the absorption of bodily fluids. Such absorbent products are available in different types, designs, and dimensions, each one having one or more unique features. For example, training pants, baby diapers, adult diapers, and incontinence guards are products designed for the containment of urine and excrement. There are other types of disposable absorbent articles, such as feminine hygiene products (e.g., heavy and light incontinence pads, pantyliners, etc.) that are designed to contain and absorb urine and/or menses by female wearers. Another type of absorbent article includes underpads configured to absorb and collect body fluid discharge from a person who may be generally confined to a bed or chair, or may otherwise be immobilized.

Currently known absorbent products typically include some form of attachment means for securing the product to a wearer's body. For example, the attachment means generally include tabs mounted on a rear section of the absorbent article, designed to be pulled forward and engaged with a front section of the article when the article (undergarment) is put in place on a wearer. The tabs typically include fasteners, such as hook-and-loop fasteners, hook-and-pile fasteners, or touch fasteners. For example, a tab may include the hook portion (or the loop portion) of a hook-and-loop fastener, while the corresponding loop portion (or hook portion) is positioned on a section of the product. Some tabs may rely on an adhesive means of attachment, such as fastening tapes, configured to engage corresponding landing zones provided on a section of the product (marked zones for application of the fastening tape).

While such fasteners tend to provide some form of attachment between different sections of an absorbent article (e.g., attachment between rear and front sections of undergarment), current fastening systems have drawbacks.

For example, in hook-and-loop fastener assemblies, the hook portions (generally positioned on the tabs), or the loop portions, may be formed from materials that are relatively stiff and inelastic and thus may cause discomfort during use. Furthermore, the corresponding loop portion must be placed and sized appropriately on the desired section of the undergarment so as to ensure that the tab, which includes the corresponding hook portion, has sufficient placement options for accommodating the various shapes and sizes of wearers.

Some absorbent products have been introduced in which only the hook portion is utilized (on the tab) with no inclusion of a corresponding loop portion. Rather, a wearer is instructed to press the tab members against the outer chassis of the product, which may be made of a material having fibers that may catch hooks within the hook portion (e.g., a nonwoven material). However, in this product design, the hooks may not attach as securely to the outer chassis of the product as they would normally with the typical loop portion, and thus the tabs may prematurely disengage during use, causing the product to shift and/or fall off the wearer's body. Furthermore, while increasing the basis weight of the nonwoven material used in the outer product chassis may slightly improve attachment, increasing basis weight can be too costly with insufficient benefit to warrant the additional costs.

Some absorbent products rely on the use of fastening tape only, without including the landing zones. However, in such product designs, the fastening tape (provided on the tab), tends to rip or tear the outer chassis of the product during intended disengagement of the tab from the garment (e.g., when a wearer desires adjustment to the garment or removal with the intent to use again). The damage to the outer chassis may compromise the integrity and effectiveness of the product and thus will limit the product to single use, which can be costly and limiting for a wearer.

SUMMARY

The present invention provides an improved fastening system for a disposable absorbent article, specifically for absorbent articles for use with incontinent adults or children, such as adult briefs and baby diapers, hereinafter referred to as "disposable undergarments". Disposable undergarments can have various shapes and sizes, and are generally configured to be worn between an individual's legs and secured about the waist. These types of products require a fastening and refastening means to secure the product onto the body and stay in place, specifically for attaching front and rear sections of the article.

The fastening system of the present disclosure comprises fastener members in the form of micro-hooks positioned on tabs extending from the article. The tabs generally extend from a rear section of the article. The fastener members are configured to attach to an exterior surface, or outer product chassis, of the article, formed at least on a front section of the article. In particular, the disposable article may be formed from a plurality of different layers, wherein the outermost layer, hereinafter referred to as the "back sheet", is formed from a nonwoven material. The exterior surface of the nonwoven material includes naturally exposed fibers, wherein, upon contact between the fastener members and the exterior surface, the micro-hooks are configured to catch within the fibers of the nonwoven material, thereby fastening the tabs to the back sheet.

The back sheet layer is designed in such a manner so as to improve the attachment surface for the fastener members. In particular, the back sheet layer has a corrugated exterior surface, which includes a plurality of peaks and valleys. The plurality of peaks and valleys increases the overall surface area, thereby increasing the amount of fibers with which the micro-hooks may engage and, in turn, improves the potential strength of attachment between the tabs and the back sheet. In addition to improving the attachment strength, the corrugated design, which is formed along the entire back sheet covering the front section, further increases the overall attachment area available for engagement with the fastener members. In other words, the areas of the front section upon which the tabs can be placed are greatly increased, which, in turn, allows for greater flexibility in the range of body shapes and sizes that the article can fit and further improves adjustment and fitting options for any given wearer. The corrugated design may further allow for the back sheet to have a thinner profile or lower basis weight (which can provide significant cost savings). Additionally, the corrugated design may further improve the feel of the back sheet, providing a softer outer surface (e.g., higher cushion effect) for improving comfort for the user.

The corrugated pattern is achieved as a result of the manner in which the back sheet is attached to another layer of the article. In particular, the back sheet may be coupled to a fluid impervious barrier (e.g., a breathable micro-porous poly film) via a plurality of adhesive bonds, wherein each valley directly corresponds to an adhesive bonding between the back sheet layer and the fluid impervious layer and each peak directly corresponds to spacing between adhesive bonding. In some embodiments, each of the plurality of adhesive bonds may be positioned from an immediately adjacent adhesive bond in the range of approximately 1 mm to 10 mm such that the plurality of peaks are spaced apart from one another via each valley. For example, in one embodiment, each of the plurality of adhesive bonds is positioned from an immediately adjacent adhesive bond by 4 mm. The adhesive may be applied in a comb slot coat pattern, where the spacing (between the adhesive tracks) is at least two times (or greater) than the width of the adhesive track. In some embodiments, the adhesive track may be 1 mm wide and the spacing between adjacent tracks is approximately 4 mm wide.

The peaks and valleys may generally be arranged in a longitudinal pattern. It should be noted, however, that, in other embodiments, the peaks and valleys may be arranged in a various patterns and need not be limited to a longitudinal pattern. For example, in some embodiments, the peaks and valleys may be oriented in a substantially horizontal direction or a substantially diagonal direction relative to the first and second layers. In another example, the peaks and valleys may include a curved length, such as a serpentine pattern or the like, or the peaks and valleys may include a non-uniform shape and may vary along their length. Yet still, in some embodiments, different portions of the first layer may include different patterns of peaks and valleys, such that the pattern of peaks and valleys can vary throughout the entire area of the first layer. For example, some sets of peaks and valleys may extend in a first direction and other sets of peaks and valleys may extend in a second direction different than the first direction (e.g., first set oriented in a longitudinal direction parallel with length of article and second set oriented in a horizontal direction parallel with width of article). Furthermore, in some embodiments, the peaks and valleys may be intermittently formed along the first layer in such a manner that they are not continuous. Accordingly, the absorbent article of the present disclosure provides numerous advantages over currently available absorbent products, particularly in the realm of disposable undergarments. In particular, the corrugated pattern on the nonwoven back sheet provides improved attachment for one or more fastener members having micro-hooks, thereby resulting in improved closure and securement of the article to a wearer. In particular, the corrugated exterior surface of the nonwoven back sheet increases the overall surface area, thereby increasing the amount of fibers with which the micro-hooks may engage and, in turn, improves the potential strength of attachment between the tabs and the back sheet. In addition to improving the attachment strength, the corrugated design, which is formed along the entire back sheet covering the front section, further increases the areas of the front section of a disposable undergarment upon which the tabs can be placed, thereby allowing for greater flexibility in the range of body shapes and sizes that the article can fit and further improves adjustment and fitting options for any given wearer. The corrugated design may further allow for the back sheet to have a thinner profile or lower basis weight (which can provide significant cost savings). Additionally, the corrugated design may further improve the feel of the back sheet, providing a softer outer surface (e.g., higher cushion effect) for improving comfort for the user.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 2A illustrates the corrugated surface of the back sheet extending the entire length of the undergarment while FIG. 2B illustrates the corrugated surface of the back sheet limited to a front section of the undergarment.

Figure 1:
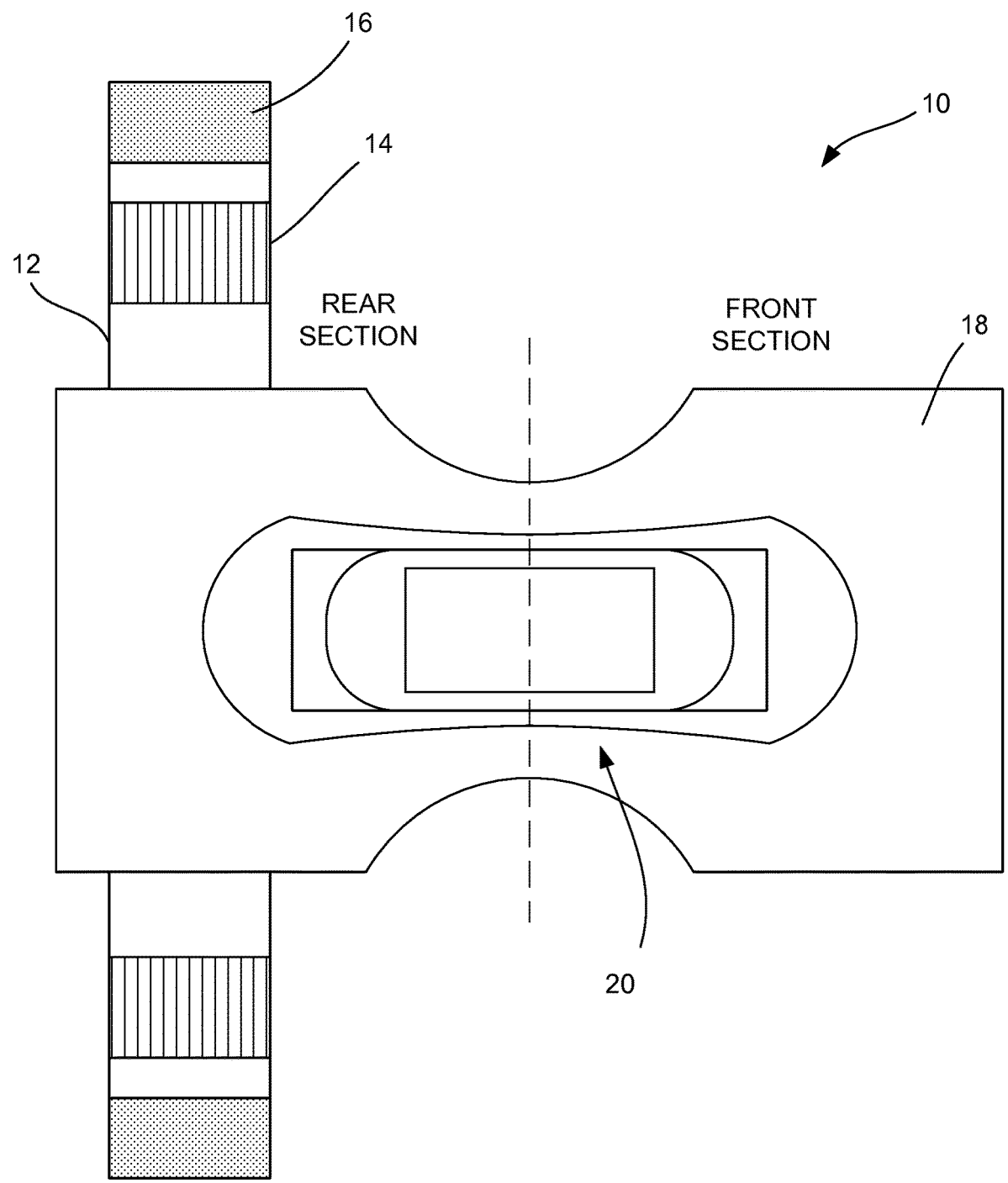
FIG. 1 is a top plan view of a disposable absorbent undergarment consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The present invention provides an improved fastening system for a disposable absorbent article, specifically for absorbent articles for use with incontinent adults or children, such as adult briefs and baby diapers, hereinafter referred to as "disposable undergarments". While the following description refers to the fastening system for use on a disposable undergarment, it should be noted that the various embodiments described herein may be used in a variety of different absorbent products, such as, for example, training pants, baby diapers, adult diapers, incontinence guards, wound care, and feminine hygiene article, and underpads, or other disposable absorbent products in which the product may be fastened to other objects, such as underlying garments, beds, furniture, and the like.

The present invention provides a disposable undergarment having an exterior surface designed to provide improved attachment for one or more fastener members thereby resulting in improved closure and securement of the undergarment to a wearer. In particular, the disposable undergarment includes fastener members in the form of micro-hooks positioned on tabs extending from undergarment, generally a rear section of the undergarment intended to be placed proximate to a wearer's buttocks. The fastener members are configured to attach to an exterior surface, or outer product chassis, of the undergarment, which is formed at least on a front section of the undergarment. In particular, the disposable undergarment may be formed from a plurality of different layers, wherein the outermost layer, hereinafter referred to as the "back sheet", is formed from a nonwoven material. The exterior surface of the nonwoven material includes naturally exposed fibers, wherein, upon contact between the fastener members and the exterior surface, the micro-hooks are configured to catch within the fibers of the nonwoven material, thereby fastening the tabs to the back sheet.

The back sheet layer is designed in such a manner so as to improve the attachment surface for the fastener members. In particular, the back sheet layer has a corrugated exterior surface, which includes a plurality of peaks and valleys. The plurality of peaks and valleys increases the overall surface area, thereby increasing the amount of fibers with which the micro-hooks may engage and, in turn, improves the potential strength of attachment between the tabs and the back sheet. In addition to improving the attachment strength, the corrugated design, which is formed along the entire back sheet covering the front section, further increases the overall attachment area available for engagement with the fastener members. In other words, the areas of the front section upon which the tabs can be placed are greatly increased, which, in turn, allows for greater flexibility in the range of body shapes and sizes that the undergarment can fit and further improves adjustment and fitting options for any given wearer. The corrugated design may further allow for the back sheet to have a thinner profile or lower basis weight (which can provide significant cost savings). Additionally, the corrugated design may further improve the feel of the back sheet, providing a softer outer surface (e.g., higher cushion effect) for improving comfort for the user.

Figure 2A:
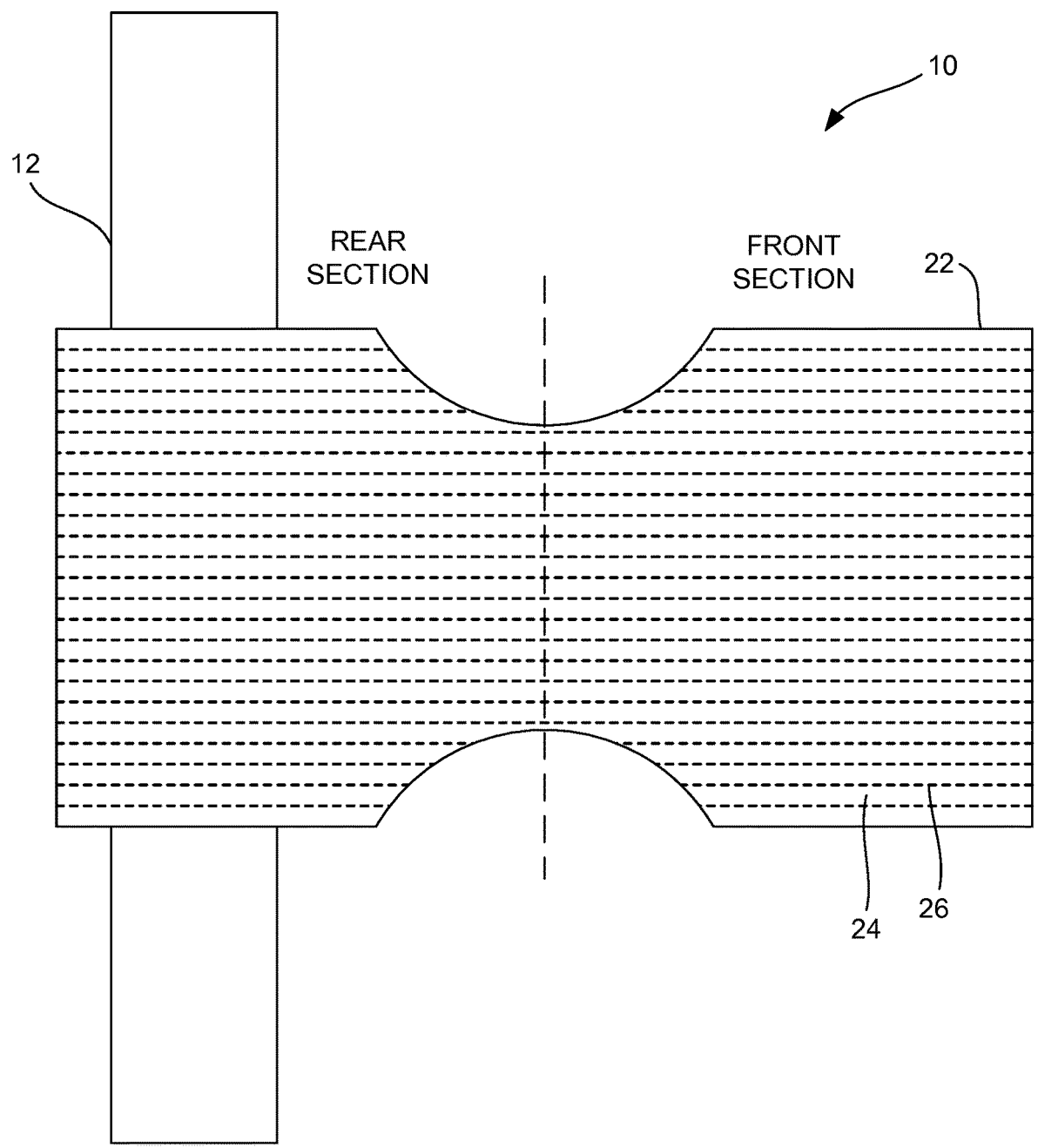
FIGS. 2A and 2B are bottom plan views of the absorbent undergarment of FIG. 1 illustrating different designs of a corrugated exterior surface of the back sheet.

FIG. 1 is a top plan view of a disposable absorbent undergarment 10 consistent with the present disclosure and FIG. 2A are bottom plan views of the absorbent undergarment 10. The undergarment 10 is generally in the form of a diaper or brief. While the following description focuses on briefs or diapers with reference to the illustrated embodiments, it should be clear that the subject invention can be used for any type of absorbent article or garment to be worn by a person for bodily fluids and/or excrement.

Figure 2B:
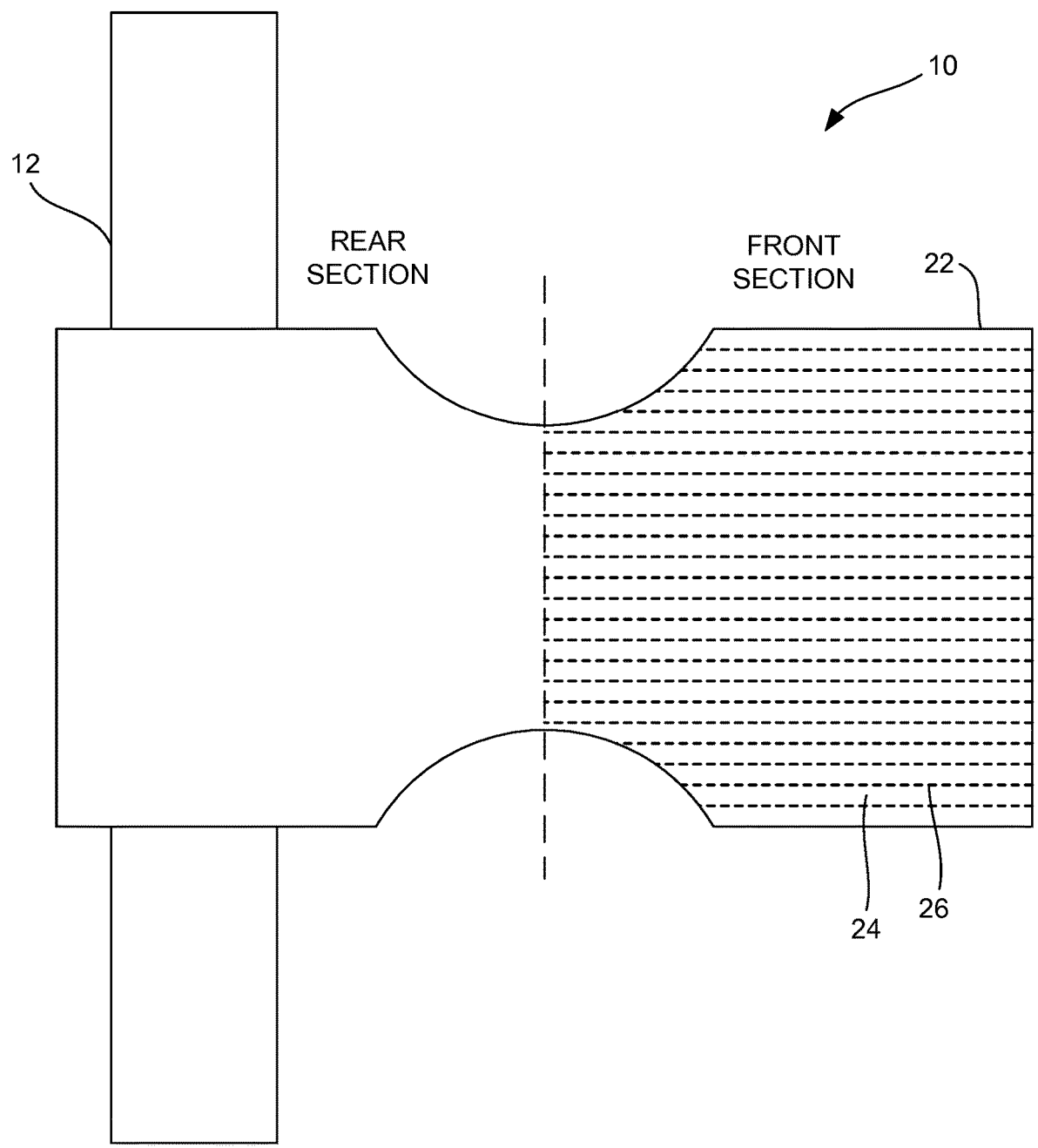

The undergarment 10 is shown in FIG. 1 from the interior side of the product that is designed to be in direct contact with the wearer, as opposed to the exterior side of the product, as shown in FIGS. 2A and 2B. The undergarment 10 generally includes a front section and a rear section, wherein the front section is generally designed to be fitted against the front, or anterior portion, of a wearer, while the rear section is generally designed to be fitted against the rear, or posterior portion, of the wearer, such that front and rear sections generally oppose one another once fitted to the wearer. The undergarment 10 can have various shapes and sizes, and is generally configured to be worn between an individual's legs and secured about the waist. In order to secure the undergarment onto a wearer's body and stay in place, the undergarment includes a fastening system. In particular, the undergarment 10 includes tabs 12 extending from the rear section of the undergarment 10. As shown, the undergarment 10 may include two tabs 12 extending from opposite sides of the rear section. Each tab 12 may include and extensible and retractable portion 14 and a fastener member 16. As will be described in greater detail herein, the fastener member 16 is configured to engage and attach to an exterior surface of the front section of the undergarment 10, thereby coupling the front and rear sections to one another and securing the undergarment onto a wearer's body.

The extensible/retractable portion 14 may generally include a stretchable material having elastic properties allowing the fastener member 16, which is generally positioned on a distal end of the tab 12, to be pulled to a desired position for attachment to the front section. Once the fastener member 16 is in place and engaged with the exterior surface of the front section, the extensible/retractable portion 14 provides a relatively constant pulling force against the fastener member 16 and the corresponding portion of the front section to which the fastener member 16 is attached, thereby further drawing the front and rear sections of the undergarment 10 towards one another to provide a secure fit against the wearer.

The undergarment 10 may be constructed from multiple layers, which may include at least a first layer 18 and a second layer 20. The first layer 18, also referred to herein as the "top sheet 18", is generally configured to contact a subject's skin and allows fluid from the subject (i.e., human, animal, etc.) to flow through it, at least in a direction away from the subject's skin. The second layer 20, also referred to herein as the "absorbent core 20", includes a fluid absorption and retention portion having at least one absorbent material for absorbing a fluid passing through the top sheet 18. In the embodiments described herein, the undergarment 10 includes at least a third layer 21, also referred to herein as the "fluid impervious barrier 21", in which the absorbent 20 is positioned between the top sheet 18 and the fluid impervious barrier 21. The fluid impervious barrier 21 may generally include a fluid impervious material, such as a poly film, and is breathable, achieved by allowing water vapor and/or air to pass through the barrier 130 while preventing the passage of liquid. It should be noted, however, that in some embodiments, the fluid impervious barrier 21 is not breathable.

The undergarment 10 further includes a fourth layer 22 coupled to the fluid impervious barrier 21. The fourth layer 22, also referred to herein as the "back sheet 22", generally serves as the outermost layer of the undergarment 10. The back sheet 22 is generally formed from a nonwoven material, to provide a more underwear-like appearance and feel, and as well as a more cost-effective and comfortable alternative to conventional disposable undergarment designs. The fibers in the nonwoven may include, for example, polypropylene, polyethylene, polyester, bi-component (polypropylene & polyethylene or polyester & polyethylene), cotton, cotton blend, viscose, rayon, etc. or a combination of different fibers. The nonwoven web may include, but is not limited to, Spunbond Polypropylene (SBPP), Spunbond-Meltblown-Spunbond (SMS), Thermal-bonded Carded Web, Spunlace, Laminate, or combinations thereof.

The fastener member 16 may include a plurality of micro-hooks or barbs which have a hook design similar to the hook portion of a hook-and-loop fastener. The exterior surface of the nonwoven material of the back sheet 22 includes exposed fibers, wherein, upon contact between the fastener member 16 and the exterior surface of the back sheet 22, the micro-hooks are configured to grab and hold onto the fibers of the nonwoven material, thereby fastening the tabs 12 to the back sheet 22.

The back sheet 22 is designed in such a manner so as to improve the attachment surface for the fastener members 16. For example, as shown in FIGS. 2A and 2B, the back sheet 22 has a corrugated exterior surface, including a plurality of peaks 24 and valleys 26. As shown in FIG. 2A, the corrugated design is provided along the entire back sheet 22 from one end of the rear section to the opposing end of the front section. It should be noted that, in some embodiments, the corrugated design may be limited to specific portions of the undergarment, such as, for example, confined to the front section only, as shown in FIG. 2B. However, in the instant embodiment described herein, the corrugated design is provided along the entire back sheet 22 layer. As will be described in greater detail herein and illustrated in subsequent figures, the plurality of peaks and valleys increases the overall surface area of the exterior surface of the back sheet 22, thereby increasing the amount of nonwoven material fibers with which the micro-hooks of the fastener members may engage and, in turn, improves the potential strength of attachment between the tabs and the back sheet.

In addition to improving the attachment strength, the corrugated design, which is may be formed along the entire back sheet 22 covering the front section, further increases the overall attachment area available for engagement with the fastener members. In other words, the areas of the front section upon which the tabs can be placed are greatly increased, which, in turn, allows for greater flexibility in the range of body shapes and sizes that the undergarment 10 can fit and further improves adjustment and fitting options for any given wearer. The corrugated design may further allow for the back sheet to have a thinner profile or lower basis weight (which can provide significant cost savings). For example, the back sheet 22 may have a basis weight in the range of approximately 15 gsm to 60 gsm. In one embodiment, the back sheet 22 includes a SBPP nonwoven having a basis weight of approximately 15 gsm. Additionally, the corrugated design may further improve the feel of the back sheet 22, providing a softer outer surface (e.g., higher cushion effect) for improving comfort for the user.

While the corrugated design of the back sheet is shown to include substantially longitudinal peaks and valleys, it should be noted that, in other embodiments, the peaks and valleys may be arranged in a various patterns and need not be limited to a longitudinal pattern. For example, in some embodiments, the peaks and valleys may be oriented in a substantially horizontal direction or a substantially diagonal direction. Yet still, in some embodiments, different portions of the back sheet may include different patterns of peaks and valleys, such that the pattern of peaks and valleys can vary throughout the entire area of the back sheet. For example, some sets of peaks and valleys may extend in a first direction and other sets of peaks and valleys may extend in a second direction different than the first direction (e.g., first set oriented in a longitudinal direction parallel with length of undergarment and second set oriented in a horizontal direction parallel with width of undergarment). Furthermore, in some embodiments, the peaks and valleys may be intermittently formed along the back sheet in such a manner that they are not continuous.

Figure 3:
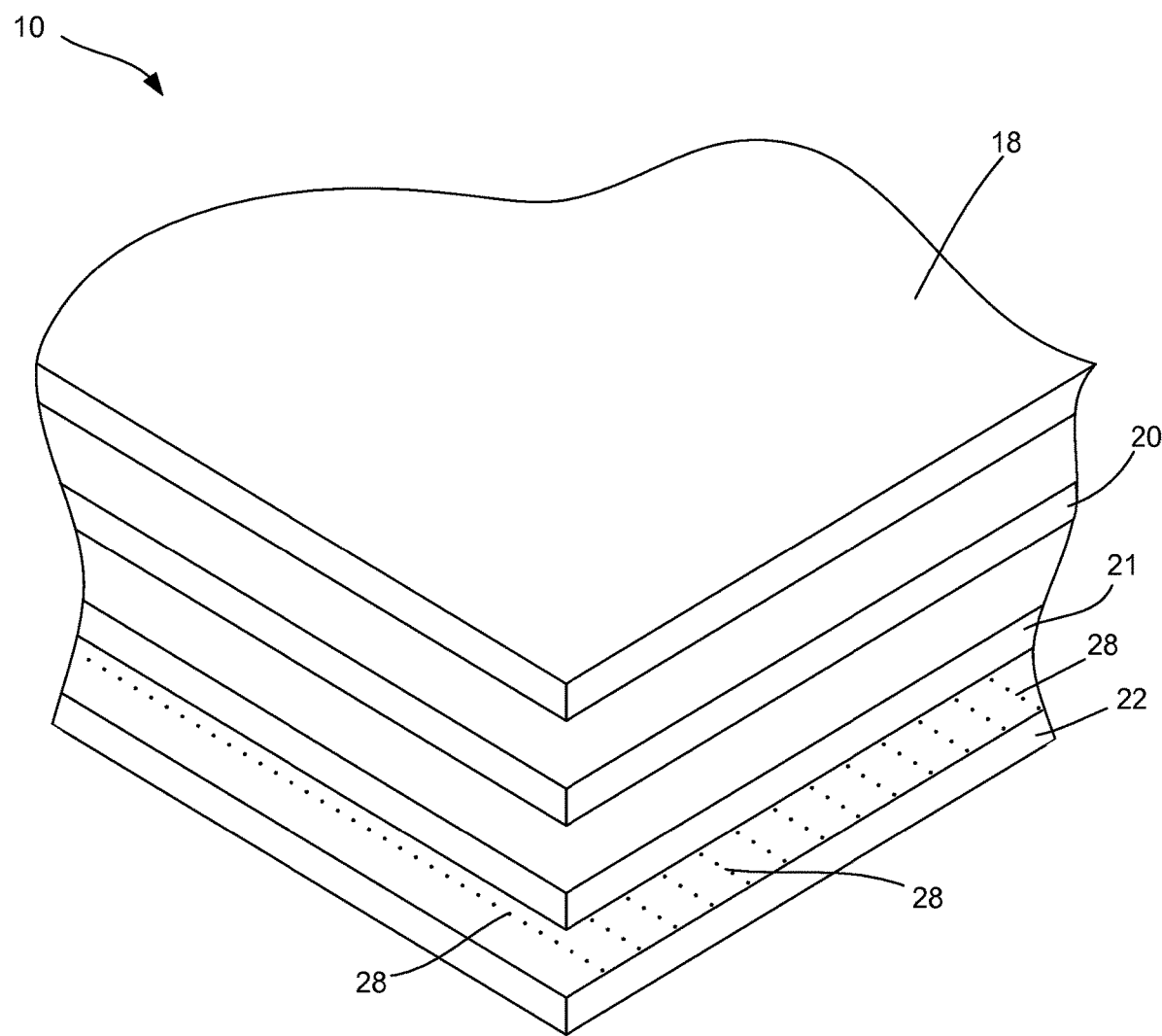
FIG. 3 is an enlarged perspective view of a portion of the absorbent undergarment of FIG. 1 illustrating the multiple layers separated from one another.

The corrugated pattern is achieved as a result of the manner in which the back sheet 22 is attached to the fluid impervious barrier 21. FIG. 3 is an enlarged perspective view of a portion of the absorbent undergarment 10 illustrating the multiple layers separated from one another. As shown, the fluid impervious barrier layer 21 and the back sheet 22 are joined together via a plurality of adhesive bonds or beads 28. The plurality of adhesive beads 28 may be arranged in a parallel pattern relative to one another along a length of the fluid impervious barrier layer 21 and back sheet 22, for example. The particular adhesive bead layout results in a plurality of peaks 24 and valleys 26 that are adjacent and substantially parallel to one another and extend along the length of the back sheet 22, which is shown in greater detail in FIGS. 4-6. In particular, each valley directly corresponds to an adhesive bonding between the back sheet layer and the fluid impervious layer and each peak directly corresponds to spacing between adjacent adhesive bonds. The particular details of the peaks and valleys and adhesive bonding will be described in greater detail herein with reference to FIGS. 5 and 6.

Figure 4:
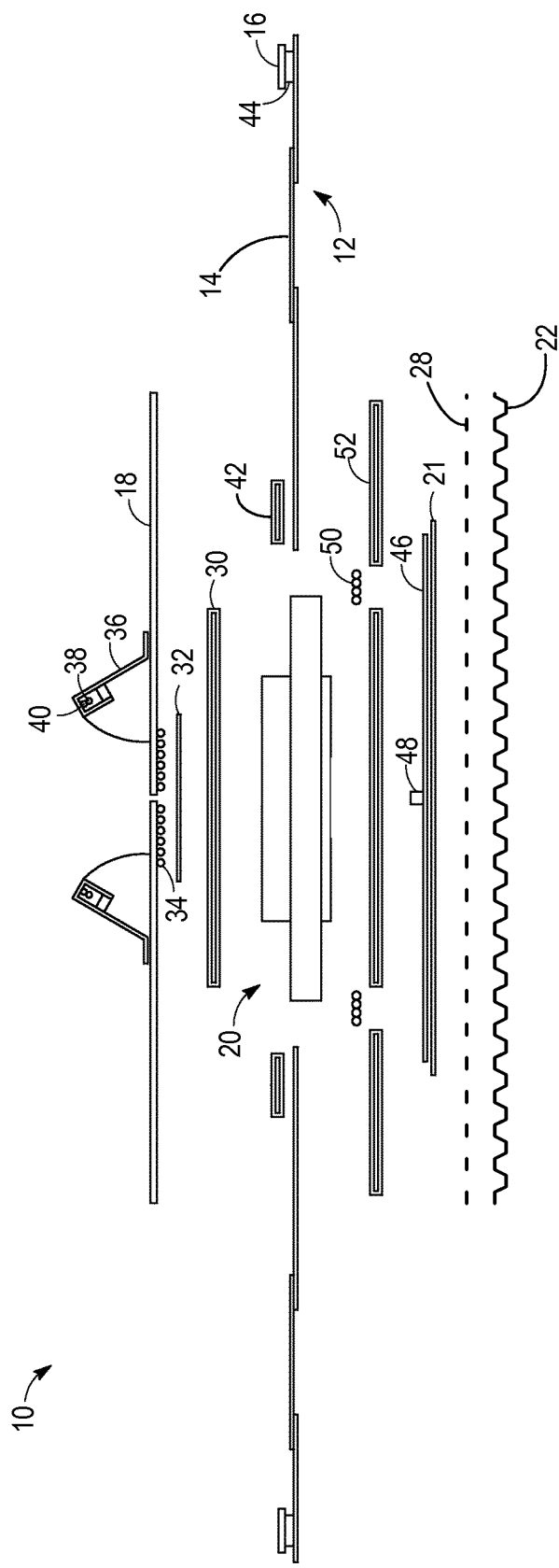
FIG. 4 is an exploded cross-sectional view of the absorbent undergarment of FIG. 1 illustrating the multiple layers and absorbent core, as well as the corrugated nonwoven back sheet.

FIG. 4 is an exploded cross-sectional view of the absorbent undergarment 10 illustrating the multiple layers, including the top sheet 18, absorbent core 20, fluid impervious barrier layer 21, and corrugated nonwoven back sheet 22.

The top sheet 18 may be joined to the absorbent core 20 via an core adhesive 30 and/or an acquisition/distribution layer 32 (ADL), such as with a corresponding ADL adhesive 34, which can be positioned between the top sheet 18 and absorbent core 20. In some embodiments, the top sheet 18 includes at least one of a nonwoven material, a hydrophilic or partially hydrophilic material, a nonwoven material with a zone-coated surfactant, and a nonwoven and apertured film. One material that can be used for the top sheet is an SBPP (Spunbond Polypropylene) hydrophilic nonwoven, commercially available from Avgol, located in Tel Aviv, Israel. The surfactant on the top sheet 18 can be zone-coated, for example, which may provide a barrier along particular portions (e.g., the sides) of the undergarment 10 to reduce fluid leakage. Optionally, the undergarment 10 may include a stand-up leg elastic assembly 36, including a nonwoven material, one or more elastic components 38, and an adhesive 40.

The undergarment 10 may further include tab attachment means 42 for coupling the tabs 12 to the undergarment 10. The attachment means 42 may include, but is not limited to, an adhesive, an ultrasonic bond, a breakable fastener, or other means of securely attaching non-woven, laminate, polymeric, or other materials. Furthermore, the fastener 16 (e.g., micro-hooks) may be fastened to the distal end of the tab 12 via an adhesive 44 or other fastening means.

The absorbent core 20 may generally include an absorbent material, a nonabsorbent material, and a combination thereof. For example, the absorbent core 20 may include one or more of: "pulp only" core; "pulp & SAP" core; "pulp & SAP & tissue" core; "airlaid composite" core; "airlaid composite" core with cotton fibers; "rayon viscose" core; "rayon viscose & pulp" core; "rayon viscose & SAP" core; "rayon viscose & pulp & SAP" core; "rayon viscose & pulp & SAP & tissue" core; "tissue" core; "tissue & SAP" core; "creped tissue or paper towel" core; "creped tissue with SAP" core; "pulp & curly fiber" core; "pulp & curly fiber &

SAP" core; SAP and nonwoven composite core (Pulpless); and "pulp & curly fiber & SAP & tissue" core.

The absorbent core 20 may be comprised of multiple layers or structures. For example, as shown, the absorbent core may include at least three absorbent core structures. Optionally, more than three core structures can be used. Optionally, one or more core structures can be used, and the one or more core structures can have a variable thickness, or can have non-homogeneously-distributed constituent parts. For example, a unitary but non-homogenous core structure can have a portion that comprises fluff without SAP and another portion that comprises fluff with SAP, and optionally another portion that comprises fluff with a different proportion of SAP relative to fluff. The multicore design of the absorbent core 20 is discussed in co-pending international application titled "Multi-Core Absorbent Article", having application no. PCT/US2016/012710, and filed Jan. 8, 2016, the content of which is incorporated by reference herein in its entirety.

The nonwoven back sheet 22 may generally extend over all or at least a portion of the undergarment 10, wherein the back sheet 22 provides a garment-facing surface of the undergarment when the undergarment is worn under clothing. As previously described, the back sheet 22 is jointed to the fluid impervious barrier 21 via adhesive bonding or beads 28.

The fluid impervious barrier layer 21 may be breathable in some embodiments, while in other embodiments, the barrier 21 is not breathable. Additionally, the barrier 21 can be cloth-like or non-cloth-like. For example, a cloth-like material for the barrier 21 a Poly Laminate, from Berry Plastics located in Chippewa Falls, WI One poly film that can be used for the barrier 21 is a polyethylene/polypropylene film blend available from Berry Plastics located in Chippewa Falls, WI One breathable poly film that can be used for the barrier 21 is a micro-porous film available from Clopay located in Mason, Ohio. One breathable cloth-like material for the barrier 130 that can be used is Poly Laminate available from Galaxy, China.

The undergarment may optionally include printing 46 over all or a portion of the surface of one or both of the nonwoven back sheet 22 or the polymeric barrier layer 21. The printing can include graphic designs, size indicia, or other markings for aesthetic or functional purposes.

Figure 5:
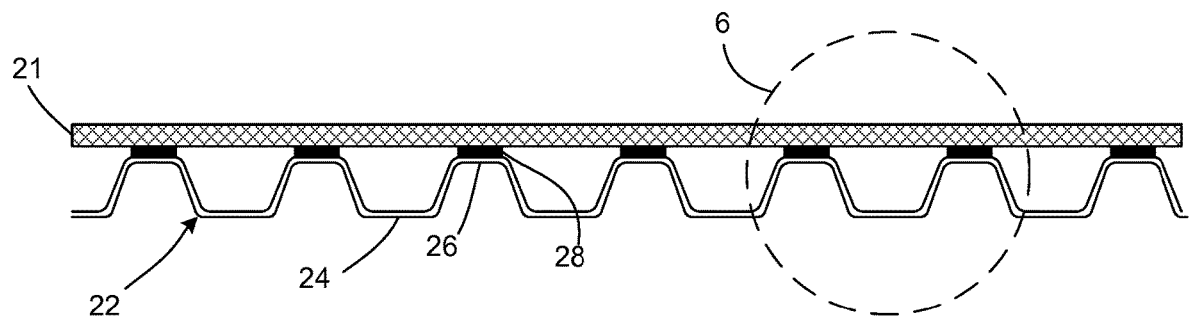
FIG. 5 is a cross-sectional view of a portion of the absorbent undergarment of FIG. 1 illustrating the corrugated nonwoven back sheet coupled to the poly film layer by way of the adhesive bonds applied in a comb slot coat pattern.
Figure 6:
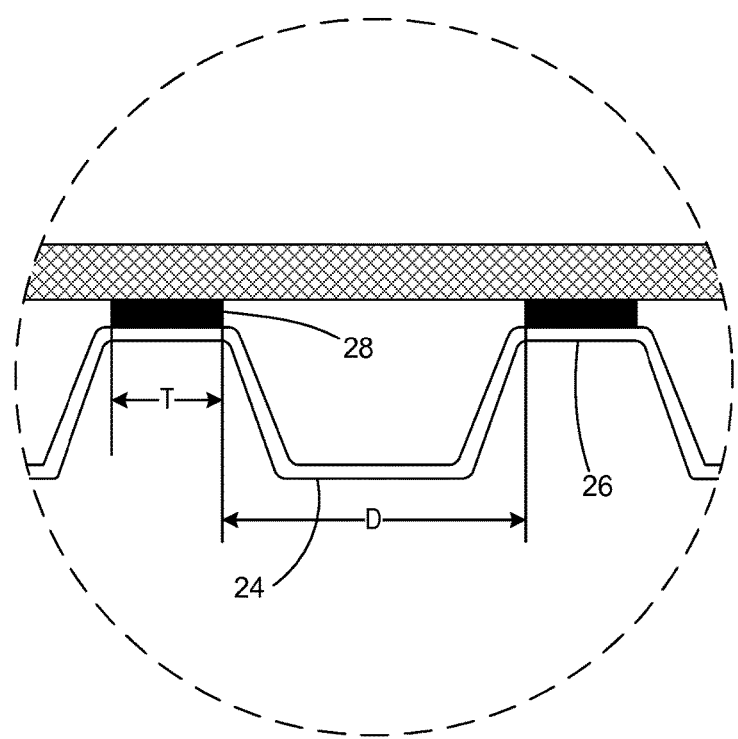
FIG. 6 is an enlarged cross-sectional view of the absorbent undergarment illustrating the multiple peaks and valleys of the back sheet layer created by the glue/adhesive bond pattern coupling the back sheet layer and the poly film layer together.

The undergarment may optionally include a wetness indicator 48, such as can be positioned substantially centrally along a portion of a length of the undergarment. Leg elastics 50 and leg elastic adhesives 52 may be layered between any two or more of the nonwoven back sheet 22, the polymeric barrier layer 21, and respective left and right side tabs 12. The leg elastics 50 may extend substantially parallel to a longitudinal axis of the undergarment 10 at or near leg cutouts. As previously described, the corrugated pattern of the exterior surface of the nonwoven back sheet 22 is achieved as a result of the manner in which the back sheet 22 is attached to the fluid impervious barrier 21. FIGS. 5 and 6 are cross-sectional views of a portion of the absorbent undergarment 10 illustrating the corrugated design, particularly, the multiple peaks and valleys of the back sheet formed as a result of the adhesive bond pattern used to join the fluid impervious barrier layer 21 with the back sheet 22. As shown, each valley 26 directly corresponds to an adhesive bead 28 between the back sheet 22 and the fluid impervious barrier layer 21, while each peak 24 directly corresponds to spacing between adhesive beads 28. For example, each adhesive bead 28 may have a thickness T of approximately 1 mm, for example, and may be spaced apart from an immediately adjacent adhesive bead 28 by a distance D, which may be approximately between 1 mm and 5 mm, for example. Accordingly, the plurality of longitudinal peaks 24 and valleys 26 are generally formed as a result of the particular adhesive bead pattern.

In some embodiments, each of the plurality of adhesive beads may be positioned from an immediately adjacent adhesive bead in the range of approximately 1 mm to 10 mm, such that the plurality of peaks are spaced apart from one another via each valley. For example, in one embodiment, each of the plurality of adhesive beads 28 is positioned from an immediately adjacent adhesive bead 28 by 4 mm. The adhesive may be applied in a comb slot coat pattern, where the spacing (between the adhesive beads or tracks) is at least two times (or greater) than the width of the adhesive bead or track. In some embodiments, the adhesive track may be 1 mm wide and the spacing between adjacent tracks is approximately 4 mm wide.

The disposable absorbent undergarment 10 of the present disclosure provides numerous advantages over currently available absorbent products, particularly in the realm of disposable undergarments. In particular, the corrugated pattern on the nonwoven back sheet provides improved attachment for one or more fastener members having micro-hooks, thereby resulting in improved closure and securement of the undergarment to a wearer. In particular, the corrugated exterior surface of the nonwoven back sheet increases the overall surface area, thereby increasing the amount of fibers with which the micro-hooks may engage and, in turn, improves the potential strength of attachment between the tabs and the back sheet. In addition to improving the attachment strength, the corrugated design, which is formed along the entire back sheet covering the front section, further increases the areas of the front section of a disposable undergarment upon which the tabs can be placed, thereby allowing for greater flexibility in the range of body shapes and sizes that the undergarment can fit and further improves adjustment and fitting options for any given wearer. The corrugated design may further allow for the back sheet to have a thinner profile or lower basis weight (which can provide significant cost savings). Additionally, the corrugated design may further improve the feel of the back sheet, providing a softer outer surface (e.g., higher cushion effect) for improving comfort for the user.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof

The invention claimed is:

1. A disposable absorbent undergarment comprising:
   an undergarment body extending along a longitudinal axis, said undergarment body comprising a rear section configured to be positioned against a subject's posterior and a front section configured to be positioned against the subject's anterior, said undergarment body comprising a back sheet formed of a nonwoven material and providing an outermost layer of the undergarment, said back sheet having a corrugated surface comprising a plurality of peaks and valleys, said peaks having flat tops, wherein said flat tops are defined by at least two opposite edges, and wherein the valleys of the back sheet are coupled to an immediately adjacent inner layer of the undergarment body via a plurality of adhesive elongate tracks extending substantially parallel to the longitudinal axis, and
   at least one side panel assembly extending from the rear section of the undergarment body away from the longitudinal axis, the side panel assembly comprising a fastener mechanism or mechanisms including a plurality of micro-hooks configured to releasably attach to the peaks of the corrugated surface of the back sheet to thereby couple the rear section of the undergarment body to the front section of the undergarment body for securing the undergarment to the subject, wherein the valleys correspond to the adhesive elongate tracks that are applied in a comb slot coat pattern, wherein a spacing between the adhesive tracks is at least two times greater than a width of the adhesive track and wherein the adhesive tracks and peaks extend substantially parallel to each other.

2. The disposable absorbent undergarment of claim 1, wherein each of the plurality of adhesive tracks is positioned from an immediately adjacent adhesive track in the range of approximately 1 mm to 10 mm such that the plurality of peaks are spaced apart from one another via each valley.

3. The disposable absorbent undergarment of claim 1, wherein each adhesive track extends an entire length of the back sheet and inner layer.

4. The disposable absorbent undergarment of claim 1, wherein at least one of the adhesive bonds is intermittently disposed between the back sheet and inner layer.

5. The disposable absorbent undergarment of claim 1, wherein the plurality of peaks and valleys increases the surface area of the nonwoven material of the back sheet thereby improving the overall potential for strength of attachment between the micro-hooks of the fastener mechanism and fiber of the nonwoven material.

6. The disposable absorbent undergarment of claim 1, wherein the back sheet has a basis weight in the range of approximately 10 gsm to 60 gsm.

7. The disposable absorbent undergarment of claim 1, wherein the inner layer is a fluid impervious barrier layer comprising a fluid impervious material.

8. The disposable absorbent undergarment of claim 7, wherein the undergarment body further comprises:
   a top sheet configured to engage a subject's skin, the top sheet comprising a breathable and fluid permeable material configured to absorb fluid and provide a degree of compression against the subject's skin; and
   an absorbent core coupled to the top sheet and comprising an absorbent material for absorbing a fluid passing through the top sheet,
   wherein the absorbent core is coupled between the top sheet and the fluid impervious barrier layer.

9. The disposable absorbent undergarment of claim 1, wherein a first surface of the back sheet is bonded to the inner layer and wherein a second surface of the back sheet is disposed opposite the first surface and includes fibers that are naturally exposed.

10. The disposable absorbent undergarment of claim 9, wherein the micro-hooks are configured to engage with the fibers.

11. The disposable absorbent undergarment of claim 1, wherein the fastener mechanism or mechanisms is fixedly coupled to at least one of the front section and the rear section by an elastic member.

12. The disposable absorbent undergarment of claim 1, wherein the peaks and valleys are arranged so that different portions of the back sheet include different patterns of peaks and valleys.

13. The disposable absorbent undergarment of claim 1, wherein the peaks and valleys form patterns not limited to a longitudinal pattern.

14. The disposable absorbent undergarment of claim 1, wherein the corrugated surface of the back sheet extends only in the front section of the undergarment.

15. A disposable absorbent undergarment comprising:
    an undergarment body extending along a longitudinal axis, said undergarment body comprising a rear section configured to be positioned against a subject's posterior and a front section configured to be positioned against the subject's anterior, wherein the undergarment body comprises a back sheet formed of a nonwoven material and providing an outermost layer of the undergarment,
    wherein the back sheet has a corrugated surface comprising a plurality of peaks and valleys, said plurality of peaks and valleys being formed as a result of a serpentine pattern of adhesive elongated tracks having curved lengths, said elongated adhesive tracks used to couple the back sheet to an inner layer of the undergarment body, so that each valley directly corresponds to an adhesive track between the back sheet and the inner layer and each peak directly corresponds to spacing between adhesive tracks; and
    at least one side panel assembly extending from the rear section of the undergarment body, the side panel assembly comprising a fastener mechanism or mechanisms including a plurality of micro-hooks configured to releasably attach to the corrugated surface of the back sheet to thereby couple the rear section of the undergarment body to the front section of the undergarment body for securing the undergarment to the subject,
    wherein the plurality of peaks and valleys are configured to increase the surface area of the nonwoven material of the back sheet and to improve the overall potential for strength of attachment between the micro-hooks of the fastener mechanism and fiber of the nonwoven material; wherein the corrugated surface of the back sheet extends along the entire length of the undergarment; wherein the peaks have flat tops, wherein each flat top forms an elongated area that is elongated in a direction parallel to the elongated tracks.

16. The disposable absorbent undergarment of claim 15, wherein the inner layer is an immediately adjacent inner layer of the undergarment body.

17. The disposable absorbent undergarment of claim 15, wherein the plurality of adhesive tracks are arranged in a substantially parallel pattern relative to one another along a length of the back sheet and inner layer such that the plurality of peaks and valleys are substantially parallel to one another and parallel to the longitudinal axis.

18. The disposable absorbent undergarment of claim 15, wherein each of the plurality of adhesive tracks is positioned from an immediately adjacent adhesive track in the range of approximately 1 mm to 10 mm such that the plurality of peaks are spaced apart from one another via each valley.

19. The disposable absorbent undergarment of claim 15, wherein each of the plurality of adhesive tracks is applied in a pattern where the spacing is at least two times greater than a width of the adhesive track.

20. The disposable absorbent undergarment of claim 15, wherein the inner layer is a fluid impervious barrier layer comprising a fluid impervious material.

21. A disposable absorbent undergarment comprising:
an undergarment body comprising:
  a rear section configured to be positioned against a subject's posterior and
  a front section configured to be positioned against the subject's anterior,
  the undergarment body comprises a back sheet formed of a nonwoven material and providing an outermost layer of the undergarment, the back sheet has a corrugated surface comprising a plurality of peaks and valleys, the back sheet is coupled to an immediately adjacent inner layer of the undergarment body via a plurality of adhesive bonds,
at least one side panel assembly extending from the rear section of the undergarment body the side panel assembly comprising a fastener mechanism or mechanisms including a plurality of micro-hooks configured to releasably attach to the corrugated surface of the back sheet to thereby couple the rear section of the undergarment body to the front section of the undergarment body for securing the undergarment to the subject;
wherein each peak of the plurality of peaks and valleys comprises a first side and a second side, both sides extending away from the back sheet toward a flat top, said flat top forming an uppermost surface of the peak;
wherein said uppermost surface defines a flat area which has the same size as or is larger than the adhesive bonds positioned adjacently to the flat peaks.

22. The disposable absorbent undergarment of claim 1, wherein the at least one side panel assembly includes an extensible and retractable portion allowing the fastener mechanism to be pulled to a desired position for attachment to the front section.

23. The disposable absorbent undergarment of claim 15, wherein the at least one side panel assembly includes an extensible and retractable portion allowing the fastener mechanism to be pulled to a desired position for attachment to the front section.

* * * * *